US00PP20786P2

(12) United States Plant Patent
Head et al.

(10) Patent No.: US PP20,786 P2
(45) Date of Patent: Feb. 23, 2010

(54) ***ILEX* PLANT NAMED 'HOGY'**

(50) Latin Name: *Ilex vomitoria*
Varietal Denomination: HOGY

(75) Inventors: William A. Head, Seneca, SC (US); Robert H. Head, Seneca, SC (US); Lisa Jones Head, Seneca, SC (US)

(73) Assignee: Head Ornamentals, Inc., Seneca, SC (US)

( * ) Notice: Subject to any disclaimer, the term of this patent is extended or adjusted under 35 U.S.C. 154(b) by 0 days.

(21) Appl. No.: 12/283,265

(22) Filed: Sep. 8, 2008

(51) Int. Cl.
*A01H 5/00* (2006.01)

(52) U.S. Cl. ..... Plt./247

(58) Field of Classification Search ..... Plt./247
See application file for complete search history.

*Primary Examiner*—Wendy C Haas
(74) *Attorney, Agent, or Firm*—C. A. Whealy

(57) ABSTRACT

A new and distinct cultivar of *Ilex* plant named 'HOGY', characterized by its compact, upright and outwardly spreading plant form; uniformly mounded habit; dense and bushy growth habit; yellowish green-colored leaves; and good garden performance.

3 Drawing Sheets

Botanical designation: *Ilex vomitoria.*
Cultivar denomination: 'HOGY'.

BACKGROUND OF THE INVENTION

The present Invention relates to a new and distinct cultivar of *Ilex*, botanically known as *Ilex vomitoria*, commercially known as dwarf yaupon holly and hereinafter referred to by the name 'HOGY'.

The new *Ilex* is a naturally-occurring branch mutation of *Ilex vomitoria* 'Nana', not patented. The new *Ilex* plant was discovered and selected by the Inventor during the spring of 1992 from within a population of plants of 'Nana' in a controlled outdoor nursery environment in Seneca, S.C.

Asexual reproduction of the new cultivar by semi-hardwood and hardwood stem cuttings in Seneca, S.C. since November, 1992 has shown that the unique features of this new *Ilex* plant are stable and reproduced true to type in successive generations of asexual reproduction.

SUMMARY OF THE INVENTION

Plants of the new *Ilex* have not been observed under all possible environmental conditions. The phenotype may vary somewhat with variations in environment such as temperature and/or light intensity without, however, any variance in genotype. The following traits have been repeatedly observed and are determined to be the unique characteristics of 'HOGY'. These characteristics in combination distinguish 'HOGY' as a new and distinct cultivar of *Ilex:*

1. Compact, upright and outwardly spreading plant form; uniformly mounded habit.
2. Dense and bushy growth habit.
3. Yellowish green-colored leaves.
4. Good garden performance.

Plants of the new *Ilex* can be compared to plants of the parent, 'Nana'. Plants of the new *Ilex* differ from plants of 'Nana' in the following characteristics:

1. Plants of the new *Ilex* are more compact than and not as vigorous as plants of 'Nana'.
2. Plants of the new *Ilex* are more uniformly mounded than plants of 'Nana'.

3. Plants of the new *Ilex* have yellow-colored leaves whereas plants of 'Nana' have green-colored leaves.

Plants of the new *Ilex* can be compared to the plants of *Ilex vomitoria* 'Stokes Dwarf', not patented. In side-by-side comparisons conducted in Seneca, S.C., plants of the new *Ilex* differed from plants of 'Stokes Dwarf' in the following characteristics:

1. Plants of the new *Ilex* are not as vigorous as plants of 'Stokes Dwarf'.
2. Plants of the new *Ilex* have yellow-colored leaves whereas plants of 'Stokes Dwarf' have green-colored leaves.

BRIEF DESCRIPTION OF THE PHOTOGRAPHS

The accompanying colored photographs illustrate the overall appearance of the new *Ilex*. These photographs show the colors as true as it is reasonably possible to obtain in colored reproductions of this type. Colors in the photographs may differ slightly from the color values cited in the detailed botanical description, which accurately describe the colors of the new *Ilex.*

The photograph on the first sheet comprises a side perspective view of a typical plant of 'HOGY' grown in an outdoor nursery.

The photograph on the second sheet is a close-up view of typical leaves of 'HOGY'.

The photograph on the third sheet is a close-up view of a typical flower of 'HOGY'.

DETAILED BOTANICAL DESCRIPTION

The aforementioned photographs and following observations and measurements describe plants grown in Seneca, S.C. in an outdoor nursery and under commercial production conditions. During the production of the plants, day temperatures ranged from −5° C. to 40° C. and night temperatures ranged from −18° C. to 35° C. Plants used for the photographs and description had been growing for twelve years. In the following description, color references are made to The Royal Horticultural Society Colour Chart, 2001 Edition, except where general terms of ordinary dictionary significance are used.

Botanical classification: *Ilex vomitoria* 'HOGY'.

Parentage: Naturally-occurring branch mutation of *Ilex vomitoria* 'Nana', not patented.

Propagation:

*Type.*—By semi-hardwood and hardwood cuttings.

*Time to initiate roots, summer.*—About 30 to 45 days at temperatures of 26° C. to 38° C.

*Time to initiate roots, winter.*—About 60 to 70 days at temperatures of 16° C. to 21° C.

*Time to produce a rooted young plant, summer.*—About 80 to 90 days at temperatures of 26° C. to 38° C.

*Time to produce a rooted young plant, summer.*—About 120 to 150 days at temperatures of 16° C. to 21 ° C.

*Root description.*—Fine, moderately fibrous; close to 161D in color.

*Rooting habit.*—Freely branching; dense.

Plant description:

*Plant form and growth habit.*—Perennial evergreen shrub; compact upright and outwardly spreading plant form; uniformly mounded habit.

*Branching habit.*—Freely branching habit; dense and bushy growth habit with numerous lateral branches developing per plant.

*Plant height.*—About 1.2 meters to 1.5 meters.

*Plant diameter, area of spread.*—About 1.8 meters to 2.1 meters.

*Lateral branch description.*—Length: About 1 cm to 4 cm. Diameter: About 1 mm to 2 mm. Internode length: About 1.5 mm to 9 mm. Strength: Strong, stiff. Texture: Puberulent. Color, young stems: Close to 59A. Color, mature stems: Close to 198A.

Foliage description: Arrangement: Alternate, simple. Length: About 1 cm to 2.5 cm. Width: About 0.5 mm to 14 mm. Shape: Ovate to elliptic. Apex: Rounded. Base: Obtuse. Margin: Serrulate. Venation pattern: Pinnate. Texture, upper and lower surfaces: Smooth, glabrous. Color: Developing leaves, upper surface: Between N144B and 1B. Developing leaves, lower surface: Close to 151D. Fully expanded leaves, upper surface: Between 7A and 151B; midvein, close to 4B; lateral veins, similar to lamina. Fully expanded leaves, lower surface: Between 144B and 11A; venation, similar to lamina. Petiole: Length: About 1 mm to 2.5 mm. Diameter: About 0.5 mm to 0.8 mm. Texture, upper and lower surfaces: Puberulent. Color, upper and lower surfaces: Close to 59A.

Flower description:

*Flower arrangement and appearance.*—Single cruciform flowers arranged in fascicles of three. Freely flowering habit; about ten flowers develop per lateral branch.

*Natural flowering season.*—Plants of the new *Ilex* typically flower during April and May in South Carolina.

*Flower longevity.*—Individual flowers last several days on the plant; flowers persistent.

*Fragrance.*—None detected.

*Flower diameter.*—About 4 mm to 5 mm.

*Flower depth.*—About 2 mm to 3 mm.

*Flower bud.*—Length: About 1 mm to 2 mm. Diameter: About 1 mm to 2 mm. Shape: Globular. Color: Close to 155C.

*Petals.*—Arrangement: Single cruciform flower form; single whorl of four petals fused at the base. Length: About 1.5 mm to 2 mm. Width: About 1 mm. Shape: Oblong. Apex: Rounded. Margin: Entire. Texture, upper and lower surfaces: Smooth, glabrous; waxy. Color: When opening and fully opened, upper surface: Close to 155C. When opening and fully opened, lower surface: Close to 155C.

*Sepals.*—Arrangement: Four fused in a single whorl; calyx, campanulate. Length: About 0.7 mm. Width: About 0.9 mm. Shape: Awl-shaped. Apex: Acute. Texture, upper and lower surfaces: Smooth, glabrous; waxy. Color: Immature, upper and lower surfaces: Close to 145B. Mature, upper and lower surfaces: Close to 145C.

*Peduncles.*—Length: About 2.5 mm to 3 mm. Diameter: About 0.2 mm to 0.5 mm. Angle: About 45° to 80° from lateral branch axis. Strength: Strong, flexible. Texture: Puberulent. Color: Close to 145B.

*Reproductive organs.*—Androecium: Not male reproductive structures observed. Gynoecium: Pistil length: About 1 mm to 1.5 mm. Stigma shape: Blunted. Stigma color: Close to 145B. Style length: About 1 mm. Style color: Close to 145B. Ovary color: Close to 145B.

*Fruits.*—Quantity per plant: About 75 to 100. Length: About 4 mm to 6 mm. Diameter: About 4 mm to 6 mm. Texture: Smooth, glabrous. Color: Close to 42B.

*Seeds.*—Quantity per fruit: About four. Length: About 2.5 mm. Diameter: About 5 mm to 6 mm. Color: Close to 150D.

Garden performance: Plants of the new *Ilex* have been observed to have good garden performance and to be tolerant to rain, wind and temperatures ranging from about −12° C. to about 45° C.

Disease/pest resistance: Plants have not been observed to be resistant to pathogens and pests common to *Ilex*.

It is claimed:

1. A new and distinct cultivar of *Ilex* plant named 'HOGY' as illustrated and described.

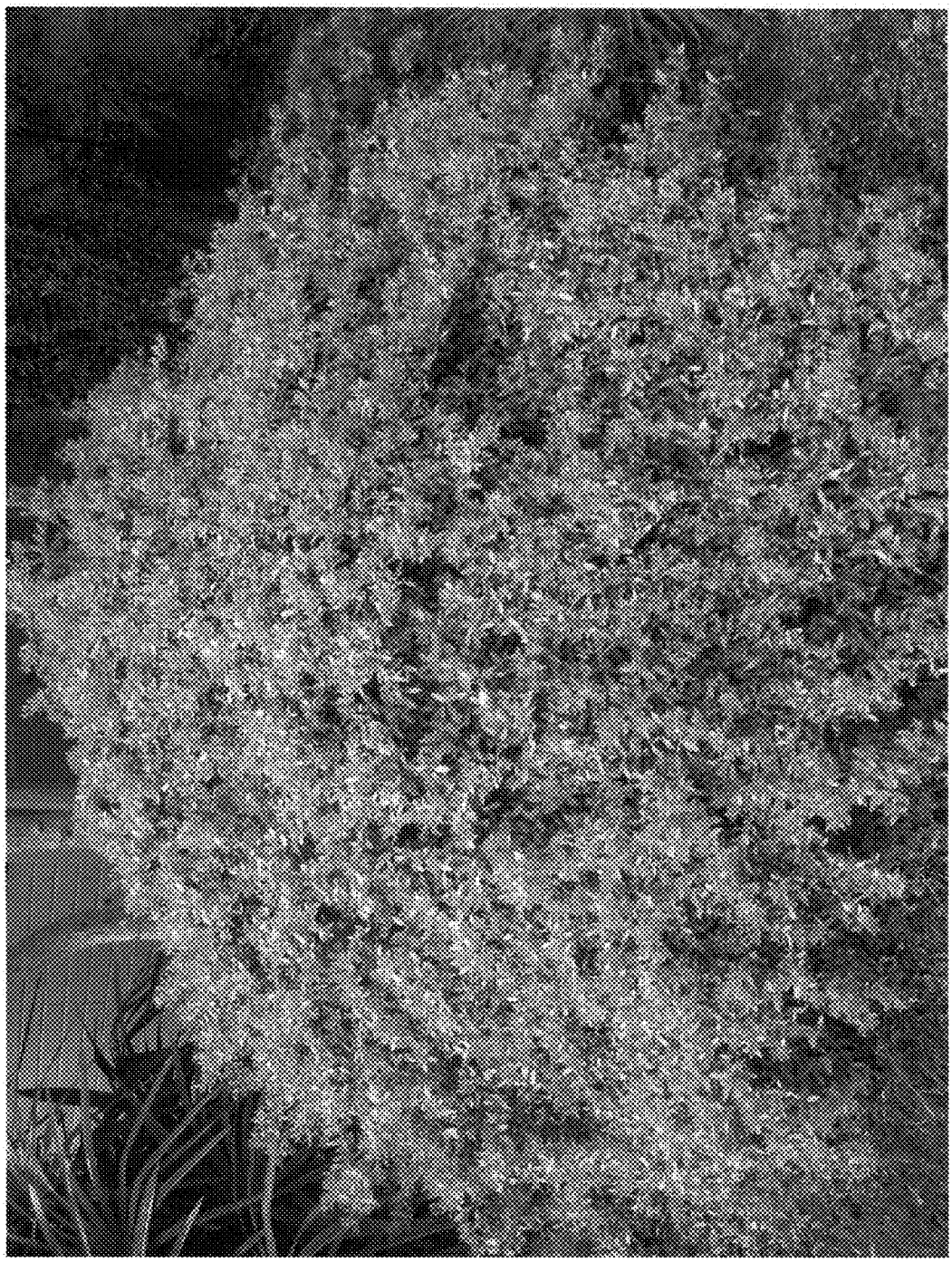

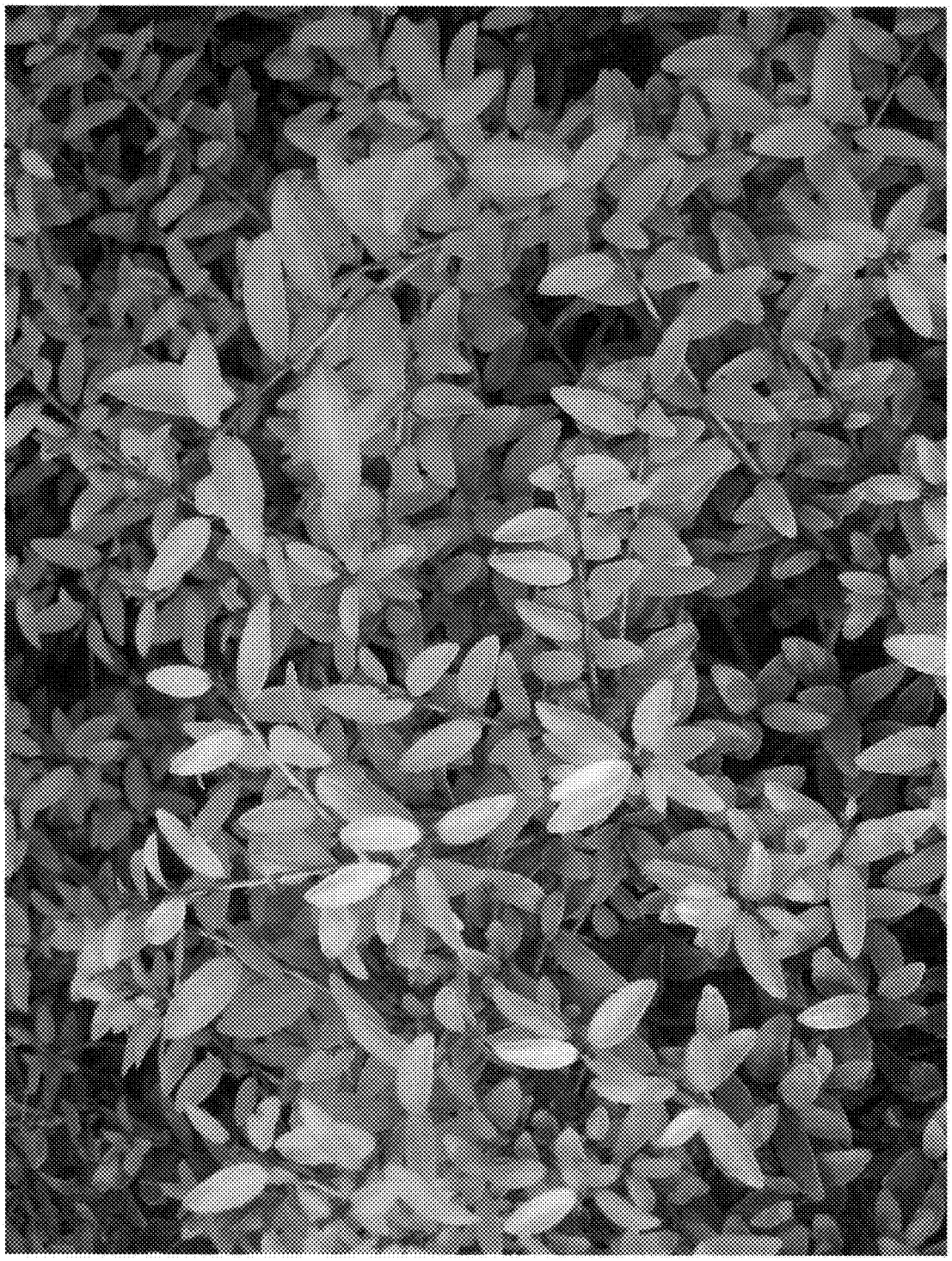

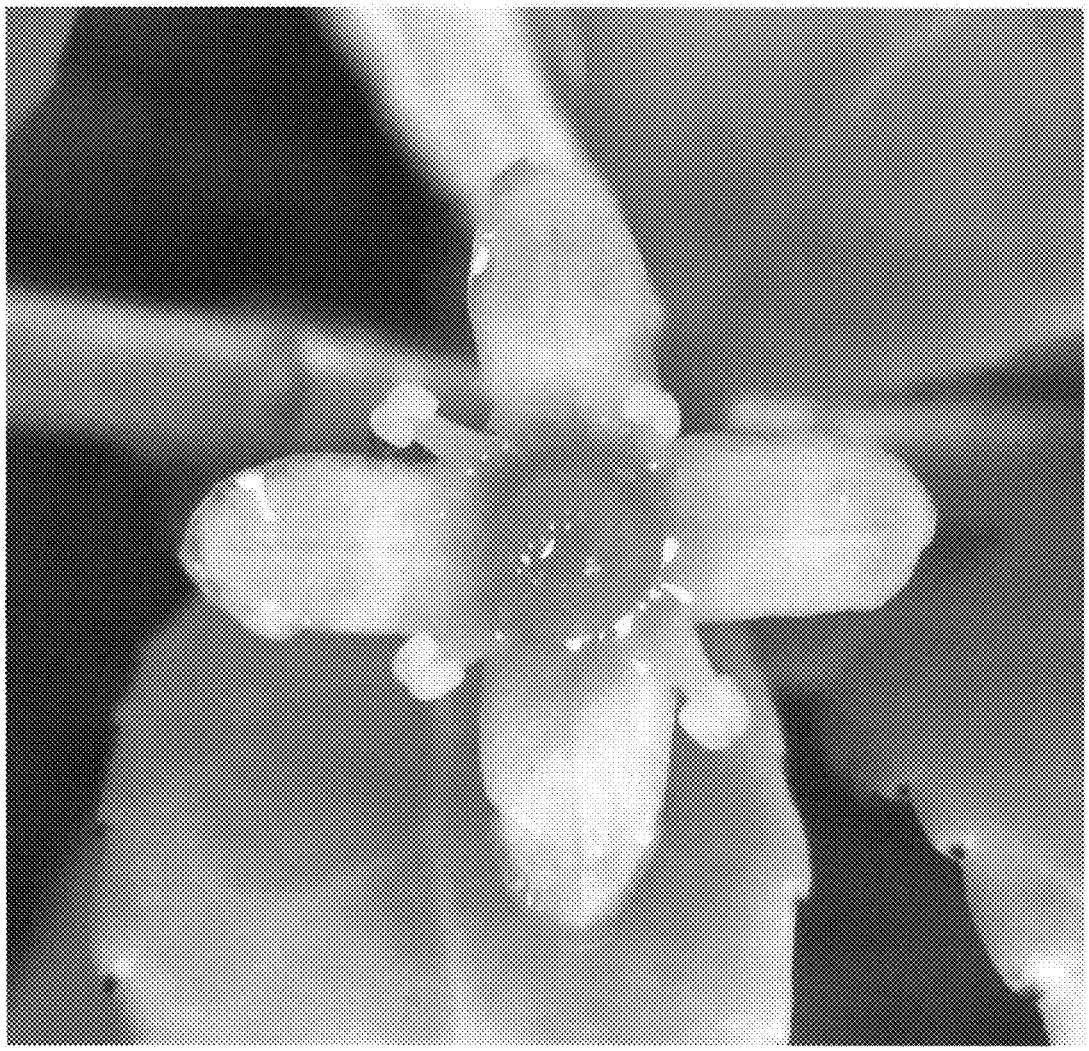

* * * * *